(12) United States Patent
Takahashi et al.

(10) Patent No.: US 9,492,422 B2
(45) Date of Patent: Nov. 15, 2016

(54) THERAPEUTIC OR PROPHYLACTIC AGENT FOR DIABETES

(75) Inventors: Takehiro Takahashi, Kamakura (JP); Hiroki Kumagai, Kamakura (JP); Takashi Kadowaki, Tokyo (JP); Naoto Kubota, Tokyo (JP); Tetsuya Kubota, Tokyo (JP)

(73) Assignees: Toray Industries, Inc. (JP); The University of Tokyo (JP)

( * ) Notice: Subject to any disclaimer, the term of this patent is extended or adjusted under 35 U.S.C. 154(b) by 36 days.

(21) Appl. No.: 13/509,483

(22) PCT Filed: Nov. 12, 2010

(86) PCT No.: PCT/JP2010/070185
§ 371 (c)(1),
(2), (4) Date: Jun. 18, 2012

(87) PCT Pub. No.: WO2011/059053
PCT Pub. Date: May 19, 2011

(65) Prior Publication Data
US 2012/0258988 A1  Oct. 11, 2012

(30) Foreign Application Priority Data
Nov. 13, 2009 (JP) .................... 2009-259544

(51) Int. Cl.
*A61K 31/5585* (2006.01)
*A61P 31/10* (2006.01)
*A61K 31/343* (2006.01)
*A61K 31/4439* (2006.01)
*A61K 31/5575* (2006.01)

(52) U.S. Cl.
CPC ......... *A61K 31/343* (2013.01); *A61K 31/4439* (2013.01); *A61K 31/5575* (2013.01)

(58) Field of Classification Search
None
See application file for complete search history.

(56) References Cited

U.S. PATENT DOCUMENTS

| | | | |
|---|---|---|---|
| 3,963,716 A | 6/1976 | Inoue et al. | |
| 4,306,075 A | 12/1981 | Aristoff | |
| 4,687,777 A | 8/1987 | Meguro et al. | |
| 5,981,594 A * | 11/1999 | Okamoto et al. | 514/573 |
| 2009/0176848 A1 * | 7/2009 | Kurumatani et al. | 514/381 |

FOREIGN PATENT DOCUMENTS

| | | |
|---|---|---|
| DE | 3 504 677 A1 | 8/1986 |
| EP | 1 894 567 A1 | 5/2008 |
| GB | 1 583 961 A | 2/1981 |
| JP | 48-097898 A | 12/1973 |
| JP | 50-70380 A | 6/1975 |
| JP | 50-070380 A | 6/1975 |
| JP | 52-136161 A | 11/1977 |
| JP | 54-095552 A | 7/1979 |
| JP | 54-130543 A | 10/1979 |
| JP | 55-000313 A | 1/1980 |
| JP | 55-022636 A | 2/1980 |
| JP | 55-057559 A | 4/1980 |
| JP | 58-219162 A | 12/1983 |
| JP | 59-137445 A | 8/1984 |
| JP | 59-141536 A | 8/1984 |
| JP | 59-157050 A | 9/1984 |
| JP | 61-030519 A | 2/1986 |
| JP | 61-267580 A | 11/1986 |
| JP | 62-286924 A | 12/1987 |
| JP | 1053672 B | 11/1989 |
| JP | 2-167227 A | 6/1990 |
| JP | 3-005457 A | 1/1991 |
| JP | 3-246252 A | 11/1991 |
| JP | 10-251146 A | 9/1998 |
| JP | 2001-512478 A | 8/2001 |
| JP | 2006-199694 A | 8/2006 |
| JP | 2006-523668 A | 10/2006 |
| JP | 2007-191494 A | 8/2007 |
| JP | 2007-536229 A | 12/2007 |
| JP | 2008-530097 A | 8/2008 |
| WO | 99/13880 A1 | 3/1999 |
| WO | 00/07992 A1 | 2/2000 |
| WO | 02/088084 A1 | 11/2002 |
| WO | 2006/034510 A2 | 3/2006 |

OTHER PUBLICATIONS

Asano et al. (Journal of the Japan Diabetes Society, 1994, vol. 37 No. 5, pp. 379-382, abstract only).*
Nakagawa et al. (Journal of the Japan Diabetes Society, 1998, vol. 41 No. 11, pp. 989-994, abstract only).*
Nishimura et al. (Journal of Diabetes and its Complications, 1995, vol. 9 No. 4, pp. 330-333, abstract only).*
Miyazaki et al. (Diabetes Care, vol. 25, No. 3, Mar. 2002).*
Raef, H. et al., "Adding Rosiglitazone to Metformin in Patients with Type 2 Diabetes: Effect on Diabetes Control and Metabolic Parameters," *International Journal of Diabetes Mellitus*, Apr. 2009, vol. 1, No. 1, pp. 2-6.

(Continued)

*Primary Examiner* — Kortney L Klinkel
*Assistant Examiner* — William Lee
(74) *Attorney, Agent, or Firm* — DLA Piper LLP (US)

(57) ABSTRACT

A therapeutic or prophylactic agent for diabetes includes a thiazolidine derivative as a PPAR-γ agonist as an effective component which exhibits a reduced side effect of the PPAR-γ agonist. The therapeutic or prophylactic agent for diabetes includes a particular IP agonist such as beraprost sodium (BPS), and a thiazolidine derivative such as pioglitazone or a pharmaceutically acceptable salt thereof. Since the therapeutic or prophylactic agent exhibits a sufficiently effective hypoglycemic action without being accompanied by side effects characteristic to PPAR-γ agonists, the agent is useful as a highly safe and effective therapeutic or prophylactic agent for diabetes.

4 Claims, No Drawings

(56) References Cited

OTHER PUBLICATIONS

Giuseppe Paolisso et al., Low-Dose Iloprost Infusion Improves Insulin Action in Aged Healthy Subjects and NIDDM Patients,: Diabetes Care, vol. 18, No. 2, Feb. 1, 1995, pp. 200-205.

Masayuki Miyata et al., "Protective Effect of Beraprost Sodium, a Stable Prostacyclin Analogue, in Development of Monocrotaline-Induced Pulmonary Hypertension," Journal of Cardiovascular Pharmacology, vol. 27, Issue 1, Jan. 1996, pp. 20-26.

Hidetoshi Hashida et al., "Beneficial Hemodynamic Effects of Oral Prostacyclin (PG12) Analogue, Beraprost Sodium, on a Patient with Primary Pulmonary Hypertension: A Case Report," Angiology, vol. 49, 1998, pp. 161-164.

Hisanori Wakita et al., "Total Synthesis of Optically Active $m$-Phenylene $PGI_2$ Derivative: Beraprost," Heterocycles, vol. 53, No. 5, 2000, pp. 1085-1110.

Ezequiel Balmori Melian et al., "Beraprost: A Review of its Pharmacology and Therapeutic Efficacy in the Treatment of Peripheral Arterial Disease and Pulmonary Arterial Hypertension," Drugs, vol. 62, 2002, pp. 107-133.

\* cited by examiner

THERAPEUTIC OR PROPHYLACTIC AGENT FOR DIABETES

RELATED APPLICATIONS

This is a §371 of International Application No. PCT/JP2010/070185, with an international filing date of Nov. 12, 2010 (WO 2011/059053 A1, published May 19, 2011), which is based on Japanese Patent Application No. 2009-259544, filed Nov. 13, 2009, the subject matter of which is incorporated by reference.

TECHNICAL FIELD

This disclosure relates to a therapeutic or prophylactic agent for diabetes, with a reduced side effect.

BACKGROUND

Diabetes is a group of diseases whose main symptom is chronic hyperglycemia accompanied by insufficiency of the action of insulin, and involves various characteristic metabolic disorders. The number of patients suffering from diabetes is increasing and, due to changes in lifestyle such as consumption of high-fat diets and lack of exercise, patients suffering from type 2 diabetes, which is a diseased state associated with risk factors such as obesity, hypertriglyceridemia, low HDL cholesteremia, glucose metabolism disorder and/or hypertension and occurs with the metabolic syndrome, are especially increasing. Since it is known that insulin resistance (insufficiency of the action of insulin) is strongly involved in the increase in the number of patients, development of a therapeutic agent for type 2 diabetes having an action that improves insulin resistance has been especially strongly demanded.

Peroxisome proliferator-activated receptor gamma (PPAR-γ) agonists, which are nuclear receptors, are recently developed therapeutic agents for type 2 diabetes, and known to improve insulin resistance and thereby exert a hypoglycemic action, which is effective for prophylaxis and therapy of diabetes.

As PPAR-γ agonists, only pioglitazone hydrochloride and rosiglitazone maleate are currently commercially available, but agents such as Isaglitazone, Rivoglitazone, Bardoxolone, Aleglitazar, Lobeglitazone, ZYH-1, AVE-0897, Chiglitazar, THR-0921, GFT-505, Indeglitazar, GSK-376501 and Inoglitazone are now being developed and drawing attention as agents effective for therapy of type 2 diabetes.

On the other hand, since PPAR-γ agonists are likely to cause characteristic side effects such as edema and body weight gain, their use is restricted. For example, PPAR-γ agonists cannot be used for patients suffering from heart failure and patients with a history of heart failure, and body weight needs to be appropriately controlled. Since obesity is one of the risk factors for diabetes, body weight gain is a side effect which diabetics want to avoid, so that reduction of the side effects of PPAR-γ agonists has been strongly demanded.

In view of this, a method has been disclosed in which a highly safe and effective therapeutic effect for diabetes is exhibited by using a PPAR-γ agonist in combination with another therapeutic agent or prophylactic agent for diabetes having a different action mechanism (e.g., α-glycosidase inhibitor, sulfonylurea agent, biguanide, aldose reductase inhibitor, statin compound, squalene synthesis inhibitor, fibrate compound, LDL catabolism promoter or angiotensin converting enzyme inhibitor) (JP 2007-191494 A).

It has been disclosed that an IP agonist such as a prostaglandin $I_2$ derivative has the actions of vasodilation, platelet aggregation inhibition, smooth-muscle proliferation inhibition, vascular endothelium protection and inflammatory cytokine inhibition and is effective as a therapeutic agent for diabetes in cases where it is used alone (JP 2-167227 A, Paolisso et al., Diabetes Care, 18, 200-205, 1995), and that an IP agonist is effective for therapy or prophylaxis of diabetes when combined with a PPAR-γ agonist (JP 2006-199694 A). However, in JP '694, the PPAR-γ agonist is merely listed as one of many arbitrary components and there is no particular description suggesting or supporting a combined effect with an IP agonist. Further, the fact that cicletanine, which is known as an endogenous prostacyclin inducer, exerts a synergistic therapeutic effect for diabetes when used in combination with a PPAR-γ agonist (Japanese Translated PCT Patent Application Laid-open No. 2006-523668), and expected matters on lipid metabolism, control of edema and reduction of hepatotoxicity of PPAR-γ agonists are described (WO 2006/034510). However, these reports do not describe that an IP agonist suppresses body weight gain due to a PPAR-γ agonist.

An IP agonist beraprost sodium has been widely employed as an orally-available stable prostaglandin $I_2$ derivative for basic research and clinical applications, to be used as a therapeutic agent for chronic artery obstruction (Melian et al., Drugs, 62, 107-133, 2002) or primary pulmonary hypertension (Hashida et al., Angiology, 49, 161-164, 1998 and Miyata et al., J. Cardiovasc. Pharmacol., 27, 20-26, 1996). Since beraprost sodium and its derivatives have a platelet aggregation inhibition action, they are suggested as having possibilities to be useful as antithrombotic agents, and also reported to have an anti-hyperlipemic action (JP 1-53672 B and JP 62-286924 A). Further, it has been discovered that beraprost sodium is effective for diabetic complications such as arterial sclerosis, diabetic nephropathy, diabetic microangiopathy, diabetic neuropathy, diabetic retinopathy and diabetic macroangiopathy (WO 99/13880), and that the combination of beraprost sodium and an antidiabetic drug enables amelioration of decrease in the functions of the motor nerve and the sensory nerve, which have not been able to be sufficiently treated with conventional antidiabetic drugs, by improvement of the nerve conduction velocity. In view of this, a therapeutic method for diabetic neuropathy using the combination of these drugs is disclosed (JP 10-251146 A). However, the target diseases are different in these reports, and the reports do not describe a therapeutic effect for diabetes by the combination of beraprost sodium and an antidiabetic drug. Further, it is disclosed that beraprost sodium is effective for therapy or prophylaxis of diabetes when it is used in combination with pioglitazone hydrochloride (JP '694), but beraprost sodium and pioglitazone hydrochloride are merely listed as one of many combinations of IP agonist drugs and PPAR-γ agonist drugs, and there is no particular description suggesting or supporting the combined effect.

However, it has not been known so far that IP agonists can be therapeutic agents or prophylactic agents which not only suppress the side effect of PPAR-γ agonists, that is, the body weight-increasing action, but also have an excellent hypoglycemic action It could therefore be helpful to provide a therapeutic or prophylactic agent for diabetes comprising as an effective component a PPAR-γ agonist, which agent exhibits a reduced side effect of the PPAR-γ agonist.

SUMMARY

We discovered that, by employing an IP agonist at a dose at which no effective hypoglycemic action is exerted in combination with a PPAR-γ agonist at a dose at which no effective hypoglycemic action is exerted, but characteristic side effects, especially an action to increase the body weight, occur, a sufficiently effective hypoglycemic action and glucose tolerance-improving action, which are not exerted by single-agent administration of each of these agents, are exerted and the side effects of the PPAR-γ agonist can be reduced.

We thus provide:
(1) A therapeutic or prophylactic agent for diabetes, comprising a combination of an IP agonist and a PPAR-γ agonist.
(2) The therapeutic or prophylactic agent according to (1), wherein the IP agonist is a prostaglandin $I_2$ derivative represented by Formula (I):

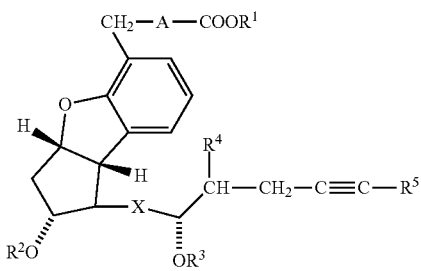

(wherein
$R^1$ represents a pharmaceutically acceptable cation or hydrogen;
$R^2$ represents hydrogen or $C_2$-$C_{10}$ acyl;
$R^3$ represents hydrogen or $C_2$-$C_{10}$ acyl;
$R^4$ represents hydrogen, methyl or ethyl;
$R^5$ represents $C_1$-$C_5$ linear alkyl;
A represents
  i) —$CH_2$—$CH_2$—; or
  ii) trans —CH=CH—; and
X represents trans —CH=CH—).
(3) The therapeutic or prophylactic agent according to (2), wherein the prostaglandin $I_2$ derivative represented by Formula (I) is beraprost sodium.
(4) The therapeutic or prophylactic agent according to any of (1) to (3), wherein the PPAR-γ agonist is a thiazolidine derivative.
(5) The therapeutic or prophylactic agent according to (4), wherein the thiazolidine derivative is pioglitazone or a pharmaceutically acceptable salt thereof.
(6) The therapeutic or prophylactic agent according to any of (1) to (5), wherein each of the IP agonist and PPAR-γ agonist is used at a dose at which a therapeutic or prophylactic effect for diabetes is not exerted by single-agent administration thereof.

Further, the following aspects of the above description are preferred:
(1)' A therapeutic or prophylactic agent for diabetes, comprising a combination of a prostaglandin $I_2$ derivative represented by Formula (I):

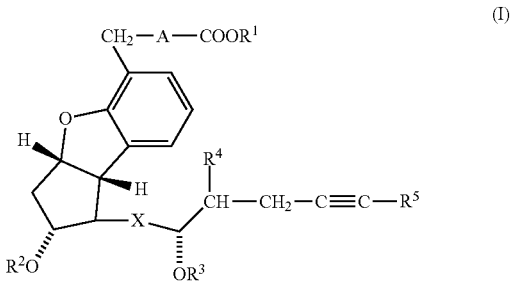

(wherein
$R^1$ represents a pharmaceutically acceptable cation or hydrogen;
$R^2$ represents hydrogen or $C_2$-$C_{10}$ acyl;
$R^3$ represents hydrogen or $C_2$-$C_{10}$ acyl;
$R^4$ represents hydrogen, methyl or ethyl;
$R^5$ represents $C_1$-$C_5$ linear alkyl;
A represents
  i) —$CH_2$—$CH_2$—; or
  ii) trans —CH=CH—; and
X represents trans —H=CH—)
and a thiazolidine derivative.
(2)' The therapeutic or prophylactic agent according to (1)', wherein, in the Formula (I), both $R^2$ and $R^3$ are hydrogen, both $R^4$ and $R^5$ are methyl, and A is —$CH_2$—$CH_2$—.
(3)' The therapeutic or prophylactic agent according to (2)', wherein the prostaglandin $I_2$ derivative represented by Formula (I) is beraprost sodium.
(4)' The therapeutic or prophylactic agent according to any of (1)' to (3)', wherein the thiazolidine derivative is pioglitazone or a pharmaceutically acceptable salt thereof.

Since the therapeutic or prophylactic agent exhibits a sufficiently effective hypoglycemic action and glucose tolerance-improving action without causing side effects characteristic to PPAR-γ agonists (e.g., body weight gain), the agent is useful as a highly safe and effective therapeutic or prophylactic agent for diabetes.

DETAILED DESCRIPTION

"IP agonist" is a general term for agents which bind to prostaglandin $I_2$ (IP) receptors on the cell membrane to exert actions such as vasodilation, platelet aggregation inhibition, smooth-muscle proliferation inhibition, vascular endothelium protection and inflammatory cytokine inhibition. The IP agonist is preferably a prostaglandin $I_2$ derivative represented by the Formula (I), and the IP agonist is especially preferably beraprost, which is a compound described in JP 1-53672 B, or beraprost sodium, which is the sodium salt thereof; or Compound 1:

Compound 1

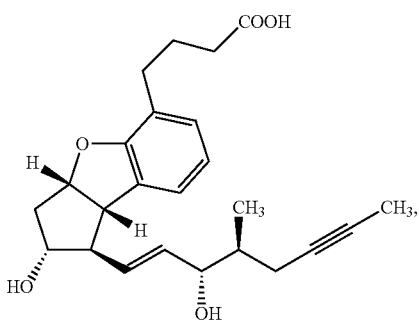

which is an isomer constituting beraprost, or Compound 2:

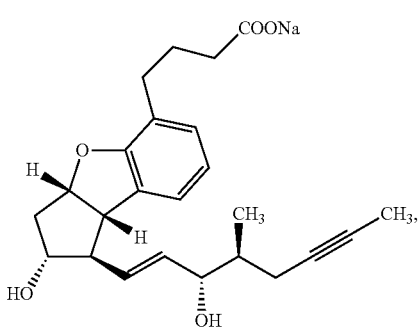

which is the sodium salt thereof.

The prostaglandin $I_2$ derivatives represented by the Formula (I) include d-isomers, l-isomers and dl-isomers, and also include mixtures of compounds represented by the Formula (I).

Preferred examples of the IP agonist also include octimibate (DE 3504677 B) and the compounds described in this specification; ataprost (JP 54-130543 A) and the compounds described in this publication; CS-570 (JP 54-95552 A) and the compounds described in this publication; cicaprost (JP 59-157050 A) and the compounds described in this publication; OP-2507 (JP 61-30519 A) and the compounds described in this publication; clinprost (JP 59-137445 A) and the compounds described in this publication; pimilprost (JP 59-141536 A) and the compounds described in this publication; TY-11223 (JP 03-246252 A) and the compounds described in this publication; samixogrel (JP 03-005457 A) and the compounds described in this publication; epoprostenol sodium (JP 52-136161 A) and the compounds described in this publication; treprostinil sodium (U.S. Pat. No. 4,306,075 B) and the compounds described in this specification; iloprost (JP 55-057559 A) and the compounds described in this publication; ibudilast(JP 48-097898 A) and the compounds described in this publication; ozagrel sodium (JP 55-000313 A) and the compounds described in this publication; isbogrel (JP 58-219162 A) and the compounds described in this publication; TRA-418 (WO 00/07992) and the compounds described in this literature; phthalazinol (JP 50-70380 A) and the compounds described in this publication; and NS-304 (WO 02/088084) and the compounds described in this literature. Either a single type or a combination of 2 or more types of IP agonist(s) may be used.

In the prostaglandin $I_2$ derivatives represented by the Formula (I), examples of the "pharmaceutically acceptable cation" include metal cations and amine cations.

The metal cations are those induced from alkaline metals (e.g., lithium, sodium and potassium) and alkaline earth metals (e.g., magnesium and calcium). Cations induced from other metals such as aluminum, zinc and iron are, of course, included.

The amine cations are those induced from primary amines, secondary amines and tertiary amines. Examples of suitable amines include: (1) aliphatic, alicyclic and aromatic amines and heterocyclic amines, such as methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, 1-methylpiperidine, 4-ethylmorpholine, 1-isopropylpyrrolidine, 2-methylpyrrolidine, 1,4-dimethylpiperazine and 2-methylpiperidine; (2) water-soluble amines and amines having a hydrophilic group(s), such as mono-ethanolamine, di-ethanolamine, tri-ethanolamine, ethyldiethanolamine, N-butylethanolamine, 2-amino-1-butanol, 2-amino-2-ethyl-1,3-propanediol, tris (hydroxymethyl)aminomethane and N-phenylethanolamine; and (3) basic amino acids, such as lysine and arginine.

The "$C_1$-$C_5$ linear alkyl" is methyl, ethyl, propyl, butyl or pentyl. Examples of the "$C_2$-$C_{12}$ acyl" include acetyl, propionyl, pentanoyl, hexanoyl and decanoyl.

Prostaglandin $I_2$ derivatives represented by the Formula (I), especially beraprost sodium, are preferred among IP agonists. Since beraprost sodium is physicochemically stable for a long period and has high oral bioavailability, effective therapy of diabetes can be realized by use of beraprost sodium in combination. Further, since beraprost sodium has been used in many clinical cases, its long-term safety in administration to humans has been established so that beraprost sodium is especially preferably used.

Beraprost sodium is already commercially available and its production method is well known. Beraprost sodium can be produced by, for example, the method described in JP 1-53672 B. Further, a commercially available beraprost sodium may also be preferably used. Beraprost sodium is normally used together with a pharmaceutically acceptable carrier or vehicle, in the form of a common oral pharmaceutical formulation such as a tablet, capsule, powder, granules or liquid, but the dosage form is not restricted thereto.

Prostaglandin $I_2$ derivatives represented by Formula (I) other than beraprost sodium can also be produced by, for example, the method described in JP 1-53672 B.

Compounds 1 and 2 can be produced by, for example, the method described in known literature (Heterocycles, Vol. 53, No. 5, p. 1085-1110, 2000) or a salification method which is commonly used. These are normally used together with a pharmaceutically acceptable carrier or vehicle, in the form of a common oral pharmaceutical formulation such as a tablet, capsule, powder, granules or liquid, but the form is not restricted thereto.

"PPAR-γ agonist" is a general term for agents which act on a nuclear receptor, peroxisome proliferator-activated receptor gamma (PPAR-γ), to enhance the insulin sensitivity. Preferred examples of the PPAR-γ agonist include pioglitazone hydrochloride and rosiglitazone maleate, which are currently commercially available; and Isaglitazone, Rivoglitazone, Bardoxolone, Aleglitazar, Lobeglitazone, ZYH-1, AVE-0897, Chiglitazar, THR-0921, GFT-505, Indeglitazar, GSK-376501 and Inoglitazone, which are currently being developed. Among PPAR-γ agonists, thiazolidine derivatives are preferred. "Thiazolidine derivatives" herein means a group of compounds having thiazolidinedione as a partial structure. Among thiazolidine derivatives, pioglitazone, which is a compound described in U.S. Pat. No. 4,687,777 B and commercially available, and pharmaceutically acceptable salts thereof are especially preferred. Examples of the pharmaceutically acceptable salts include inorganic salts such as hydrochloric acid salt, nitric acid salt, hydrobromic acid salt, sulfuric acid salt, boric acid salt and phosphoric acid salt; organic acid salts such as acetic acid salt, maleic acid salt, fumaric acid salt, tartaric acid salt, succinic acid salt, malic acid salt, lactic acid salt, citric acid salt, malonic acid salt, benzoic acid salt, paratoluenesulfonic acid salt and methanesulfonic acid salt; and acid addition salts including those to which an amino acid such as lysine, glycine, phenylalanine, asparagine or glutamic acid is added. Either a single type or a combination of 2 or more types of PPAR-γ agonist(s) may be used.

Pioglitazone hydrochloride is an excellent insulin sensitizer and, by recovering the function of damaged insulin receptors, it normalizes the intracellular localization of glucose transporters and normalizes enzyme systems playing central roles in glucose metabolism such as glucokinase, or lipid metabolism-related enzyme systems such as lipoprotein lipase. This results in not only improvement of insulin resistance and glucose tolerance, but also reduction of neutral fat and free fatty acids. In addition, since pioglitazone hydrochloride has been used in many clinical cases, its long-term effectivity in human has been established so that pioglitazone hydrochloride is especially preferably used.

The production methods of pioglitazone and its pharmaceutically acceptable salts are well known and production can be carried out by, for example, the methods described in JP 55-22636 A and JP 61-267580 A. Commercially available products may also be preferably used. Pioglitazone or its pharmaceutically acceptable salt is normally used together with a pharmaceutically acceptable carrier or vehicle, in the form of a common oral pharmaceutical formulation such as a tablet, capsule, powder, granules or liquid, but the form is not restricted thereto.

The combination of a compound represented by the Formula (I), especially beraprost sodium, among IP agonists, and especially pioglitazone hydrochloride among PPAR-γ agonists is most preferred.

"Therapeutic or prophylactic agent for diabetes" also includes an agent which is a therapeutic agent as well as a prophylactic agent for diabetes.

The dose of the therapeutic or prophylactic agent may be determined according to the doses of the individual agents, and may be appropriately selected depending on the age, body weight and symptoms of the subject to whom the agent is to be administered; administration time; dosage form; administration method; combination of agents; and the like.

In cases where the IP agonist is used in humans, it is preferred to administer the IP agonist in an amount of, for example, 1 to 1000 μg/adult/administration, preferably 5 to 500 μg/adult/administration in terms of the amount of a prostaglandin $I_2$ derivative represented by the Formula (I) as an effective component, which is preferably administered at one time or about 2 to 4 times for not less than 1 day, especially not less than 3 days. In cases where the IP agonist is applied to a non-human mammal, the dose is preferably 0.1 μg/kg to 100 mg/kg, more preferably 1 μg/kg to 50 mg/kg in terms of the amount of a prostaglandin $I_2$ derivative represented by the Formula (I) as an effective component, which is administered at one time or dividedly in about 2 to 4 times for not less than 1 day, especially not less than 3 days.

The dose of the PPAR-γ agonist may be selected, in the case of oral administration, within the range of 0.01 to 10 mg/kg body weight, which is the clinical dose (preferably 0.05 to 10 mg/kg body weight, more preferably 0.05 to 5 mg/kg body weight), and, in the case of parenteral administration, within the range of 0.005 to 10 mg/kg body weight (preferably 0.01 to 10 mg/kg body weight, more preferably 0.01 to 1 mg/kg body weight). Administration is usually carried out 1 to 3 times a day.

Surprisingly, as described in the Examples below, an excellent therapeutic or prophylactic effect for diabetes is exerted by combined use of the IP agonist and the PPAR-γ agonist even in cases where the dose of each of these agonists is one at which a therapeutic or prophylactic effect for diabetes is not exerted by single-agent administration. In addition, although the PPAR-γ agonist causes side effects such as body weight gain even at such a dose, the IP agonist reduces the side effects of the PPAR-γ agonist. Therefore, by using the IP agonist and the PPAR-γ agonist such that each of these is administered at a dose at which a therapeutic or prophylactic effect for diabetes is not exerted by single-agent administration and at which the IP agonist reduces side effects of the PPAR-γ agonist, an excellent therapeutic or prophylactic effect can be achieved while reduction of the side effects and reduction of the cost of therapy can be achieved (reduction of the dose of the agent, of course, results in a lower cost), which is preferred. Such a dose of the IP agonist is, in the cases of oral administration, 5 to 500 μg/adult/administration, preferably 5 to 250 μg/adult/administration, which is preferably administered at one time or about 2 to 4 times for not less than 1 day, especially not less than 3 days. The dose of the PPAR-γ agonist may be selected, in the case of oral administration, within the range of 0.05 to 1.0 mg/kg body weight, preferably 0.05 to 0.5 mg/kg body weight, and, in the case of parenteral administration, within the range of 0.025 to 1.0 mg/kg body weight, preferably 0.025 to 0.5 mg/kg body weight. Administration is usually carried out 1 to 3 times a day.

The administration method is not restricted and may be selected from, for example, oral administration, subcutaneous administration, intravenous or intravascular administration, intramuscular administration, pulmonary administration, intraduodenal administration and intraperitoneal administration. A more preferred dosage form is oral administration.

The IP agonist, for example, a prostaglandin $I_2$ derivative represented by the Formula (I), may be formulated as appropriate using a pharmaceutically acceptable additive which is necessary for the formulation. More particularly, examples of a vehicle which may be contained in the formulation include sugars such as lactose, mannitol, xylitol and dextrin; starches such as corn starch, hydroxypropyl starch and partially-alphanized starch; cellulose derivatives such as crystalline cellulose, hydroxypropyl cellulose, hydroxypropyl methylcellulose and sodium carboxymethylcellulose; polyvinylpyrrolidone; polyethylene oxide 5000K; and mixtures composed of 2 or more of these. Examples of a binder which may be contained in the formulation include hydroxypropyl cellulose (HPC), hydroxypropyl methylcellulose (HPMC), methyl cellulose (MC), sodium carboxymethylcellulose (CMCNa), polyvinylpyrrolidone (PVP), polyethylene glycol (PEG), starch, Macrogol 6000, L-glutamic acid, magnesium stearate, and mixtures composed of 2 or more of these.

The IP agonist such as a formulation containing a prostaglandin $I_2$ derivative represented by the Formula (I), may be administered either orally or parenterally.

In the cases of oral administration, the prostaglandin $I_2$ derivative represented by the Formula (I) may be formulated into a tablet, powder, fine granules, granules, tablet, liquid, syrup, capsule, pill or spray. In such cases, the shaped product may be coated with a film, coated with sugar or filled in a capsule. Formulation into a tablet, fine granules, granules, powder or liquid is especially preferred. Alternatively, when a prostaglandin $I_2$ derivative represented by the Formula (I) is formulated, the effective component may be included in a food to prepare a formula meal. Such a formula meal may be in the form of a solid, semifluid or solution.

In the cases of parenteral administration, the IP agonist, such as a prostaglandin $I_2$ derivative represented by the Formula (I), may be formulated into various injection solutions or suppository. In such cases, another solute such as sodium chloride or glucose enough to make the solution isotonic may be used, or the formulation may be prepared into a sustained-release formulation by a known method such as use of a hydrogel.

The administration route of the PPAR-γ agonist is commonly oral administration. The unit dosage form is not restricted as long as it is prepared by a normal formulation technique, and examples thereof include powders, granules, tablets and capsules.

These various formulations may be prepared according to conventional methods using known auxiliary materials which may be normally used in the field of formulation of pharmaceuticals, such as vehicles, binders, disintegrators, lubricants, solubilizers, correctives and coating agents.

For example, as a carrier used for shaping into a tablet, those known in the art may be widely used, and specific examples of the carrier include vehicles such as lactose, saccharose, sodium chloride, glucose, urea, starch, calcium carbonate, kaolin, crystalline cellulose and silicic acid; binders such as water, ethanol, propanol, simple syrup, glucose solutions, starch solutions, gelatin solutions, carboxymethyl cellulose, shellac, methyl cellulose, potassium phosphate and polyvinyl pyrrolidone; disintegrators such as dry starch, sodium alginate, agar powder, laminaran powder, sodium hydrogen carbonate, calcium carbonate, polyoxyethylene sorbitan fatty acid esters, sodium lauryl sulfate, stearic acid monoglyceride, starch and lactose; disintegration suppressing agents such as saccharose, stearin, cacao butter and hydrogenated oil; absorption enhancers such as quaternary ammonium base and sodium lauryl sulfate; moisturizers such as glycerin and starch; adsorbents such as starch, lactose, kaolin, bentonite and colloidal silicic acid; and lubricants such as purified talc, stearate, boric acid powder and polyethylene glycol. The tablet may be prepared as a tablet with a normal coating, such as a sugar-coated tablet, gelatin-coated tablet, enteric-coated tablet or film-coated tablet, or a bilayer tablet or multilayer tablet.

As a carrier used for shaping into a pill, those known in the art may be widely used, and specific examples of the carrier include vehicles such as glucose, lactose, starch, cacao butter, hydrogenated vegetable oil, kaolin and talc; binders such as gum arabic powder, powdered tragacanth, gelatin and ethanol; and disintegrators such as laminaran agar. Further, as required, a coloring agent, preservative, perfume, flavoring agent, sweetener and/or another drug may be contained.

The amount of the PPAR-γ agonist contained in the pharmaceutical formulation is not restricted and may be appropriately selected from a wide range, and the amount is usually 1 to 70% by weight, preferably 1 to 30% by weight with respect to the total amount of the composition.

The therapeutic or prophylactic agent may be administered in the form of a combination drug. Alternatively, a plurality of individual agents may be administered at the same time. Alternatively, the individual agents may be administered at appropriate intervals. The intervals acceptable for allowing an effect caused by administration of the drug to be achieved can be confirmed clinically or by an animal experiment. Each single agent is formulated into a form appropriate for the compound, and then administered. The administration route may be different among the agents.

In the therapeutic or prophylactic agent, in cases where a side effect, especially body weight gain, was observed as a result of administration of a PPAR-γ agonist, the dose of the PPAR-γ agonist may be reduced as appropriate to within the range whose upper limit is a dose at which a clinically acceptable minor side effect occurs.

Further, a known antidiabetic agent may be used in combination. Examples of the known antidiabetic agent include PPAR-α agonists, PPAR-δ agonists, retinoid RXR agonists, β3-adrenaline receptor agonists, 11β-hydroxysteroid dehydrogenase inhibitors, protein tyrosine phosphatase-1B (PTP-1B) inhibitors, AMP-activated protein kinase (AMPK) activators, acetyl-CoA carboxylase (ACC) inhibitors, cannabinoid receptor 1(CB1) antagonists, insulin secretagogues (ATP-dependent potassium channel inhibitors (sulfonylurea drugs, sulfonamide drugs, phenylalanine derivatives and the like)), biguanides, α-glucosidase inhibitors, insulin formulations, insulin analogues, dipeptidyl peptidase IV inhibitors, glucagon-like peptide 1 (GLP1) agonists and GLP1. These known antidiabetic agents may also be administered in the form of a combination drug. Alternatively, a plurality of individual agents may be administered at the same time. Alternatively, the individual agents may be administered at appropriate intervals.

Examples of the method of evaluation of the therapeutic or prophylactic effect for diabetes include blood glucose measurement, the glucose tolerance test and the hyperinsulinemic euglycemic glucose clamp method, and, in particular, blood glucose measurement and the glucose tolerance test are employed as diagnostic methods for diabetes.

Our agents and methods will now be described more concretely by way of Examples below, but this disclosure is not restricted to these Examples.

EXAMPLES

Example 1

Combined Effect of Beraprost Sodium (BPS) and Pioglitazone Hydrochloride on Blood Glucose Level and Body Weight of KKAy Mice For the experiment, male KKAy mice (CLEA Japan, Inc.) were used. KKAy mice show obesity and high blood glucose from 7 or 8 weeks old, and are commonly used as model mice for type 2 diabetes. The KKAy mice were purchased when they were 5 weeks old, and, from immediately thereafter, fed with CMF feed (Oriental Yeast Co., Ltd.) for 3 weeks under free food/water intake conditions, before being subjected to the experiment. For continuous subcutaneous administration of a solvent (physiological saline, 6 µL/day) or BPS (1 mg/kg/day, commercially available product from Toray Industries, Inc.), a minipump for sustained release (Alzet micro osmotic pump model 1002, Alzet osmotic pumps company) was subcutaneously placed in each KKAy mouse. The continuous administration of physiological saline or BPS was carried out until the end of the experiment. From 3 days after the placement (beginning of the subcutaneous continuous administration), oral administration of a solvent (0.5% methyl cellulose (MC) solution, 10 mL/kg) or pioglitazone hydrochloride (product synthesized in Toray Industries, Inc.) was started. Pioglitazone hydrochloride was administered as a suspension in 0.5% MC solution. The 0.5% MC solution and pioglitazone hydrochloride were administered for 10 days, during which the administration was carried out once per day in the evening. The mice were divided into the following experimental groups:

(1) Control group (n=8): physiological saline (6 μL/day)+ 0.5% MC solution (10 mL/kg)
(2) BPS group (n=6): BPS (1 mg/kg/day)+0.5% MC solution (10 mL/kg)
(3) Pioglitazone hydrochloride 3 mg group (n=6): physiological saline (6 μL/day)+pioglitazone hydrochloride (3 mg/kg)
(4) BPS/pioglitazone hydrochloride 3 mg-combined-use group (n=6): BPS (1 mg/kg/day)+pioglitazone hydrochloride (3 mg/kg)
(5) Pioglitazone hydrochloride 30 mg group (n=6): physiological saline (6 μL/day)+pioglitazone hydrochloride (30 mg/kg).

The body weight and the casual blood glucose level were measured on the day before starting of the continuous administration of physiological saline or BPS (these correspond to the data shown in the "Before administration" columns in Tables 1 and 2). The body weight was measured when 0.5% MC solution or pioglitazone hydrochloride was finally administered, and the casual blood glucose level was measured about 18 hours after the final administration (these correspond to the data shown in the "After administration" columns in Tables 1 and 2). The casual blood glucose level was measured by collecting about 5 μL of blood from the tail vein and subjecting the blood to measurement with a simplified blood glucose meter (Medisense Precision Xceed, ABBOTT JAPAN Co., LTD.).

As a result, as shown in Table 1, the BPS group and the pioglitazone hydrochloride 3 mg group showed no change in the casual blood glucose level compared to the value observed before the beginning of drug administration. On the other hand, the BPS/pioglitazone hydro-chloride 3 mg-combined-use group and the pioglitazone hydrochloride 30 mg group showed significant decrease in the casual blood glucose level compared to the value observed before the beginning of drug administration, and the extent of the action was similar between these groups.

In terms of the action on the body weight, as shown in Table 2, the pioglitazone hydrochloride 3 mg group and the pioglitazone hydrochloride 30 mg group showed significant increase in the body weight compared to the value observed before the beginning of drug administration. On the other hand, the BPS/pioglitazone hydrochloride 3 mg-combined-use group showed no change in the body weight compared to the value observed before the beginning of drug administration.

Thus, it was revealed that, by combined administration of BPS at a dose at which a sufficiently effective hypoglycemic action is not exerted by single-agent administration and 3 mg of pioglitazone hydrochloride, an action to decrease the casual blood glucose level is exerted to almost the same extent as in the case of administration of 30 mg/kg pioglitazone hydrochloride, and the body weight-increasing action, which is observed after single-agent administration of 3 mg/kg pioglitazone hydrochloride, can be suppressed.

TABLE 1

Casual blood glucose levels observed before and after administration of drugs (in KKAy mice)

| Experiment group | Number of examples | Casual blood glucose level (mg/dL ± standard error) | |
| --- | --- | --- | --- |
| | | Before administration | After administration |
| Control | 8 | 475.3 ± 25.3 | 426.4 ± 42.0 |
| BPS | 6 | 493.0 ± 35.6 | 392.3 ± 28.9 |
| Pioglitazone hydrochloride 3 mg | 6 | 450.3 ± 15.4 | 452.8 ± 53.4 |
| Combined use of BPS/Pioglitazone hydrochloride 3 mg | 6 | 471.5 ± 26.3 | 334.2 ± 30.8** |
| Pioglitazone hydrochloride 30 mg | 6 | 437.7 ± 21.7 | 271.3 ± 16.9** |

**$p < 0.01$, paired t-test for data obtained before and after administration of each drug Each value in the table represents the mean±standard error among individuals.

TABLE 2

Body weights observed before and after administration of drugs (in KKAy mice)

| Experiment group | Number of examples | Body weight (g ± standard error) | |
| --- | --- | --- | --- |
| | | Before administration | After administration |
| Control | 8 | 42.4 ± 0.8 | 43.4 ± 1.1 |
| BPS | 6 | 41.2 ± 0.8 | 42.3 ± 1.1 |
| Pioglitazone hydrochloride 3 mg | 6 | 41.7 ± 1.2 | 44.2 ± 1.3** |
| Combined use of BPS/Pioglitazone hydrochloride 3 mg | 6 | 41.9 ± 1.2 | 43.7 ± 1.8 |
| Pioglitazone hydrochloride 30 mg | 6 | 42.6 ± 1.1 | 46.7 ± 1.3** |

**$p < 0.01$, paired t-test for data obtained before and after administration of each drug Each value in the table represents the mean±standard error among individuals.

Example 2

Combined Effect of Beraprost Sodium (BPS) and Pioglitazone Hydrochloride on Glucose Tolerance of KKAy Mice For the experiment, male KKAy mice (CLEA Japan, Inc.) were used. The KKAy mice were purchased when they were 5 or 7 weeks old, and, from immediately thereafter, fed with CMF feed (Oriental Yeast Co., Ltd.) for 2 to 4 weeks under free food/water intake conditions, before being subjected to the experiment. After dividing the mice into groups, oral administration of a solvent (0.5% methyl cellulose (MC) solution, 10 mL/kg) or pioglitazone hydrochloride (product synthesized in Toray Industries, Inc.) was started. Pioglitazone hydrochloride was administered as a suspension in 0.5% MC solution. The MC solution and pioglitazone hydrochloride were administered for 20 days, during which the administration was carried out once per day in the evening. Six days after the beginning of administration of the MC solution and pioglitazone hydrochloride, for continuous subcutaneous administration of a solvent (physiological saline, 6 μL/day) or BPS (1 mg/kg/day, commercially available product from Toray Industries, Inc.), a minipump for sustained release (Alzet micro osmotic pump model 1002, Alzet osmotic pumps company) was subcutaneously placed in each KKAy mouse. The continuous administration of physiological saline or BPS was carried out until the end of the experiment. The experimental groups were as follows:
(1) Control group (n=6): physiological saline (6 μL/day)+ 0.5% MC solution (10 mL/kg)
(2) BPS group (n=5): BPS (1 mg/kg/day)+0.5% MC solution (10 mL/kg)
(3) Pioglitazone hydrochloride 3 mg group (n=5): physiological saline (6 μL/day)+pioglitazone hydrochloride (3 mg/kg)
(4) BPS/pioglitazone hydrochloride 3 mg-combined-use group (n=6): BPS (1 mg/kg/day)+pioglitazone hydrochloride (3 mg/kg)
(5) Pioglitazone hydrochloride 30 mg group (n=6): physiological saline (6 μL/day)+pioglitazone hydrochloride (30 mg/kg).

After the final oral administration of 0.5% MC solution and pioglitazone hydrochloride, a glucose tolerance test was carried out. This glucose tolerance test was carried out by fasting the mice for not less than 17 hours and performing forced oral administration of an aqueous glucose solution (1.5 g/10 mL/kg) under unanesthetized conditions. The blood glucose level was measured immediately before the administration of glucose (this timing is regarded as "0 minute") and 15, 30, 60 and 120 minutes after the administration of glucose. The blood glucose level was measured by collecting about 5 μL of blood from the tail vein and subjecting the blood to measurement with a simplified blood glucose meter (Glutest Ace R, ARKRAY, Inc./Sanwa Kagaku Kenkyusho Co., Ltd.). The increase in the blood glucose level at each timing relative to the blood glucose level observed immediately before the administration of glucose (0 minute) was defined as Δblood glucose level. The length of time (minutes) after the administration of glucose was plotted along the abscissa and Δblood glucose level (mg/dL) was plotted along the ordinate, to calculate the area under the Δblood glucose level-time curve from 0 minute to 120 minutes ($\Delta AUC_{0-120}$).

As a result, as shown in Table 3, the BPS group and the pioglitazone hydrochloride 3 mg group showed no change in $\Delta AUC_{0-120}$ compared to the control group. On the other hand, the BPS/pioglitazone hydrochloride 3 mg-combined-use group showed significant decrease in $\Delta AUC_{0-120}$ compared to the control group, so that a glucose tolerance-improving action was observed. The amount of decrease in the value was significantly larger than that observed in the pioglitazone hydrochloride 30 mg group.

Thus, it was revealed that, by combined use of BPS and pioglitazone hydrochloride, each at a dose at which a hypoglycemic action is not exerted by single-agent administration, a glucose tolerance-improving action is exerted in KKAy mice to almost the same or a higher extent compared to administration of 30 mg/kg pioglitazone hydrochloride, indicating that the combination exhibits a sufficient effect as a therapeutic and prophylactic agent for diabetes.

TABLE 3

The area under the Δblood glucose level-time curve ($\Delta AUC_{0-120}$) in the glucose tolerance test after administration of a drug (in KKAy mice)

| Experiment group | Number of examples | $\Delta AUC_{0-120}$ |
|---|---|---|
| Control | 6 | 26266 ± 3753 |
| BPS | 5 | 18684 ± 3551 |
| Pioglitazone hydrochloride 3 mg | 5 | 23138 ± 4870 |
| Combined use of BPS/Pioglitazone hydrochloride 3 mg | 6 | 13159 ± 2056*# |
| Pioglitazone hydrochloride 30 mg | 6 | 22461 ± 2157 |

*$p < 0.05$, t-test against the control group
$p < 0.05$, t-test against the pioglitazone hydrochloride 30 mg group Each value in the table represents the mean±standard error among individuals.

INDUSTRIAL APPLICABILITY

We confirmed that combined administration of an IP agonist, especially a prostaglandin $I_2$ derivative represented by the Formula (I), with a PPAR-γ agonist enhances the hypo-glycemic action of the PPAR-γ agonist, reduces side effects (especially body weight gain), and allows a glucose tolerance-improving action. Therefore, the therapeutic or prophylactic agent by combination of an IP agonist and a PPAR-γ agonist can be expected to be an excellent therapeutic or prophylactic agent for diabetes, in which side effects of the PPAR-γ agonist are reduced.

The invention claimed is:
1. A method of lowering blood glucose in diabetic patients comprising administering 1) a prostaglandin $I_2$ derivative represented by Formula (I):

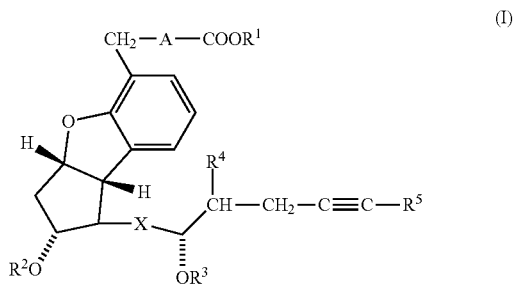

and 2) a thiazolidinedione compound selected from the group consisting of Pioglitazone, Isaglitazone, Rivoglitazone and Lobeglitazone to a mammal having diabetes, wherein,
$R^1$ represents a pharmaceutically acceptable cation or hydrogen;
$R^2$ represents hydrogen or $C_2$-$C_{10}$ acyl;
$R^3$ represents hydrogen or $C_2$-$C_{10}$ acyl;
$R^4$ represents hydrogen, methyl or ethyl;
$R^5$ represents $C_1$-$C_5$ linear alkyl;
A represents
  i) —CH$_2$—CH$_2$—; or
  ii) trans —CH=CH—; and
X represents trans —CH=CH—),
wherein the prostaglandin $I_2$ derivative is administered in an amount of 1 to 250 μg/adult/administration at 1 to 4 times a day in administration to a human and in an amount of 0.1 μg/kg to 1 mg/kg at 1 to 4 times a day in the case of administration to a non-human mammal, and the thiazolidinedione compound is administered in an amount of 0.01 to 1.0 mg/kg body weight per an adult 1 to 3 times a day for oral administration and in an amount of 0.005 to 1.0 mg/kg body weight per an adult 1 to 3 times a day for parenteral administration,
  wherein the prostaglandin $I_2$ derivative and the thiazolidinedione compound are administered in a synergistically effective amount to lower blood glucose.

2. The method according to claim 1, wherein both $R^2$ and $R^3$ are hydrogen, both $R^4$ and $R^5$ are methyl, and A is $-CH_2-CH_2-$.

3. The method according to claim 2, wherein said prostaglandin $I_2$ derivative represented by Formula (I) is beraprost sodium.

4. The method according to claim 1, wherein said thiazolidinedione compound is pioglitazone or a pharmaceutically acceptable salt thereof.

* * * * *